US012147252B2

(12) United States Patent
Malgat et al.

(10) Patent No.: US 12,147,252 B2
(45) Date of Patent: Nov. 19, 2024

(54) CARTRIDGE FOR AN AEROSOL-GENERATING SYSTEM

(71) Applicant: Philip Morris Products S.A., Neuchatel (CH)

(72) Inventors: Alexandre Malgat, Les Tuileries de Grandson (CH); Noori Moyad Brifcani, Neuchatel (CH); Rui Batista, Morges (CH); Oleg Mironov, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 16/877,198

(22) Filed: May 18, 2020

(65) Prior Publication Data

US 2020/0281269 A1    Sep. 10, 2020

Related U.S. Application Data

(63) Continuation of application No. 16/723,790, filed on Dec. 20, 2019, now Pat. No. 11,287,838, which is a
(Continued)

(30) Foreign Application Priority Data

Feb. 10, 2014 (EP) ..................................... 14154552
Feb. 10, 2014 (EP) ..................................... 14154553
Feb. 10, 2014 (EP) ..................................... 14154554

(51) Int. Cl.
*A61M 11/04* (2006.01)
*A24F 40/10* (2020.01)
(Continued)

(52) U.S. Cl.
CPC ......... *G05D 23/2401* (2013.01); *A24F 40/42* (2020.01); *A24F 40/46* (2020.01);
(Continued)

(58) Field of Classification Search
None
See application file for complete search history.

(56) References Cited

U.S. PATENT DOCUMENTS 2,057,353 A    10/1936  Whittemore, Jr. et al.
4,947,874 A    8/1990   Brooks et al.
(Continued)

FOREIGN PATENT DOCUMENTS

CN    201197360 Y    2/2009
CN    202456410 U    10/2012
(Continued)

OTHER PUBLICATIONS

International Search Report and Written Opinion of the International Searching Authority issued Aug. 4, 2015 in PCT/EP2014/077852 filed Dec. 15, 2014.
(Continued)

*Primary Examiner* — Elizabeth M Kerr
(74) *Attorney, Agent, or Firm* — Oblon, McClelland, Maier & Neustadt, L.L.P.

(57) ABSTRACT

A heater assembly for an aerosol-generating system is provided, including: an electrically insulating support having an aperture; an electrical heating element disposed across the aperture in the electrically insulating support, being configured to heat a liquid aerosol-forming substrate to form an aerosol, and being substantially flat; capillary material, wherein a portion of the capillary material is in contact with the electrical heating element, and the capillary material is configured to convey the liquid aerosol-forming substrate to the electrical heating element; and two electrical contacts respectively connected to ends of the electrical heating element, the two electrical contacts supported by the
(Continued)

electrically insulating support. An aerosol-generating system including an aerosol-generating device and a cartridge is also provided.

20 Claims, 7 Drawing Sheets

Related U.S. Application Data continuation of application No. 15/117,663, filed as application No. PCT/EP2014/077852 on Dec. 15, 2014, now Pat. No. 10,555,556.

(51) Int. Cl.
| | |
|---|---|
| *A24F 40/42* | (2020.01) |
| *A24F 40/46* | (2020.01) |
| *A24F 40/70* | (2020.01) |
| *A24F 42/80* | (2020.01) |
| *A61M 15/00* | (2006.01) |
| *A61M 15/06* | (2006.01) |
| *G05D 23/24* | (2006.01) |
| *H05B 3/06* | (2006.01) |
| *H05B 3/14* | (2006.01) |
| *H05B 3/16* | (2006.01) |
| *H05B 3/26* | (2006.01) |
| *H05B 3/34* | (2006.01) |
| *A61M 16/00* | (2006.01) |

(52) U.S. Cl.
CPC .............. *A24F 40/70* (2020.01); *A24F 42/80* (2020.01); *A61M 11/042* (2014.02); *A61M 15/06* (2013.01); *H05B 3/06* (2013.01); *H05B 3/145* (2013.01); *H05B 3/16* (2013.01); *H05B 3/265* (2013.01); *H05B 3/34* (2013.01); *H05B 3/342* (2013.01); *H05B 3/347* (2013.01); *A24F 40/10* (2020.01); *A61M 15/0021* (2014.02); *A61M 15/0043* (2014.02); *A61M 2016/0024* (2013.01); *A61M 2205/3653* (2013.01); *A61M 2205/8206* (2013.01); *H05B 2203/011* (2013.01); *H05B 2203/014* (2013.01); *H05B 2203/015* (2013.01); *H05B 2203/017* (2013.01); *H05B 2203/021* (2013.01); *H05B 2203/022* (2013.01)

(56) References Cited

U.S. PATENT DOCUMENTS

| | | | |
|---|---|---|---|
| 5,589,117 A | 12/1996 | Yang | |
| 6,155,268 A | 12/2000 | Takeuchi | |
| 6,585,509 B2 | 7/2003 | Young et al. | |
| 6,889,280 B1 | 5/2005 | Barmore | |
| 6,899,280 B2 | 5/2005 | Kotary et al. | |
| 7,888,275 B2 | 2/2011 | Ward et al. | |
| 7,920,777 B2* | 4/2011 | Rabin | A01M 1/2077 |
| | | | 122/366 |
| 8,156,944 B2 | 4/2012 | Han | |
| 8,314,591 B2 | 11/2012 | Terry et al. | |
| 8,794,231 B2 | 8/2014 | Thorens et al. | |
| 8,910,640 B2 | 12/2014 | Sears et al. | |
| 9,504,279 B2 | 11/2016 | Chen | |
| 9,943,108 B2 | 4/2018 | Lord | |
| 2005/0191481 A1 | 9/2005 | He et al. | |
| 2007/0107879 A1* | 5/2007 | Radomski | A61M 16/18 |
| | | | 165/104.26 |
| 2009/0220222 A1 | 9/2009 | Rabin et al. | |
| 2010/0242974 A1 | 9/2010 | Pan | |
| 2011/0226236 A1 | 9/2011 | Buchberger | |
| 2011/0309157 A1 | 12/2011 | Yang et al. | |
| 2012/0111346 A1 | 5/2012 | Rinker et al. | |
| 2013/0034075 A1 | 2/2013 | Zang et al. | |
| 2013/0056012 A1* | 3/2013 | Hearn | A24F 42/20 |
| | | | 131/273 |
| 2013/0160764 A1 | 6/2013 | Liu | |
| 2013/0192615 A1 | 8/2013 | Tucker et al. | |
| 2013/0213419 A1* | 8/2013 | Tucker | A24F 40/46 |
| | | | 131/328 |
| 2013/0312776 A1 | 11/2013 | Newton | |
| 2013/0319407 A1 | 12/2013 | Liu | |
| 2013/0333700 A1* | 12/2013 | Buchberger | B05B 7/0012 |
| | | | 128/203.26 |
| 2014/0123989 A1 | 5/2014 | Lamothe | |
| 2014/0150785 A1 | 6/2014 | Malik et al. | |
| 2014/0182610 A1 | 7/2014 | Liu | |
| 2014/0238422 A1 | 8/2014 | Plunkett et al. | |
| 2014/0261487 A1 | 9/2014 | Chapman et al. | |
| 2014/0283825 A1 | 9/2014 | Buchberger | |
| 2014/0299125 A1 | 10/2014 | Buchberger | |
| 2014/0305454 A1 | 10/2014 | Rinker et al. | |
| 2014/0346689 A1 | 11/2014 | Dubief | |
| 2015/0090279 A1 | 4/2015 | Chen | |
| 2015/0136156 A1 | 5/2015 | Liu | |

FOREIGN PATENT DOCUMENTS

| | | | |
|---|---|---|---|
| CN | 102861694 A | 1/2013 | |
| CN | 102939021 A | 2/2013 | |
| CN | 103338663 A | 10/2013 | |
| CN | 103491815 A | 1/2014 | |
| CN | 103932401 A | 7/2014 | |
| CN | 203986095 U | 12/2014 | |
| CN | 203986096 U | 12/2014 | |
| CN | 204070542 U | 1/2015 | |
| CN | 204317492 U | 5/2015 | |
| EA | 201100197 A1 | 3/2012 | |
| EP | 0 288 874 B1 | 3/1994 | |
| EP | 0 893 071 A1 | 1/1999 | |
| EP | 2 404 515 | 1/2012 | |
| EP | 2 460 423 A1 | 6/2012 | |
| EP | 2 606 756 A1 | 6/2013 | |
| GB | 2504076 A | 1/2014 | |
| GB | 2513638 A | 11/2014 | |
| JP | 11-89551 A | 4/1999 | |
| JP | 2013-520982 A | 6/2013 | |
| JP | 2013-545474 A | 12/2013 | |
| KR | 10-1032911 | 5/2011 | |
| KR | 10-2012-0084304 A | 7/2012 | |
| KR | 10-2013-0136677 A | 12/2013 | |
| KZ | 28 018 B | 12/2013 | |
| WO | 2008/113420 A1 | 9/2008 | |
| WO | 2009/132793 | 11/2009 | |
| WO | 2011/042212 A1 | 4/2011 | |
| WO | WO 2011/107737 A1 | 9/2011 | |
| WO | 2011/137453 A2 | 11/2011 | |
| WO | WO 2011/146316 A2 | 11/2011 | |
| WO | WO 2012/018809 A1 | 2/2012 | |
| WO | WO 2012/072790 A1 | 6/2012 | |
| WO | WO-2012085205 A1 * | 6/2012 | .......... A24B 15/167 |
| WO | WO 2013/013808 A1 | 1/2013 | |
| WO | 2013/083634 A1 | 6/2013 | |
| WO | 2013/159245 A1 | 10/2013 | |
| WO | WO 2014/004648 A1 | 1/2014 | |
| WO | WO 2014/012906 A1 | 1/2014 | |
| WO | 2014/071329 A1 | 5/2014 | |
| WO | 2014/130695 A1 | 8/2014 | |
| WO | 2014/159982 A1 | 10/2014 | |
| WO | 2014/177861 A1 | 11/2014 | |
| WO | 2015/066127 A1 | 5/2015 | |

OTHER PUBLICATIONS

Japanese Office Action issued on Aug. 20, 2018 in Patent Application No. 2016-546461, 15 pages (with English translation).
Japanese Office Action issued on Sep. 11, 2018 in Patent Application No. 2016-546461, 26 pages (with partial English translation).
European Office Action issued on Mar. 19, 2019 in Patent Application No. 14812501.6, 19 pages.

(56) References Cited

OTHER PUBLICATIONS

European Office Action issued on Mar. 22, 2019 in Patent Application No. 14812501.6, therein, 6 pages.
English translation of Russian Office Action issued on Mar. 26, 2019 in Patent Application No. 2018130815/12(050179), 7 pages.
European Office Action issued on Apr. 10, 2019 in Patent Application No. 14 812 501.6, 5 pages
Korean Office Action issued Mar. 17, 2021 in corresponding Korean Patent Application No. 10-2016-7021372 (with English translation), 15 pages.
U.S. Appl. No. 16/723,790, filed Jun. 16, 2021, 1st Office Action.
Office Action issued Jan. 27, 2023 in Korean Application No. 10-2022-7015861, along with and English translation.
Office Action issued Jan. 12, 2023 in Chinese Application No. 202010774669.1, along with an English translation.
Notice of Opposition issued May 27, 2022 in European Patent Application No. 14812501.6.
Notice of Allowance issued Mar. 11, 2022 in corresponding Korean Application No. 10-2016-7021372, along with an English translation.
Search Report issued Jun. 21, 2023 in Chinese Patent Application No. 2020107746691, along with an English translation.

* cited by examiner

CARTRIDGE FOR AN AEROSOL-GENERATING SYSTEM

CROSS-REFERENCE TO RELATED APPLICATIONS

This application is a continuation application of and claims the benefit of priority under 35 U.S.C. § 120 to U.S. application Ser. No. 16/723,790, filed on Dec. 20, 2019, which is a continuation application of and claims the benefit of priority under 35 U.S.C. § 120 to U.S. application Ser. No. 15/117,663, filed on Aug. 9, 2016, which is a U.S. National Stage application of PCT/EP2014/077852, filed on Dec. 15, 2014, and claims benefit of priority under 35 U.S.C. § 119 from European Patent Application Nos. 14154552.5, filed on Feb. 10, 2014; 14154553.3, filed on Feb. 10, 2014; and 14154554.1, filed on Feb. 10, 2014. The entire contents of each of which are incorporated herein by reference.

The present invention relates aerosol-generating systems. In particular, the invention relates to handheld aerosol-generating system, such as electrically operated smoking systems. Aspects of the invention relate to a cartridge for aerosol-generating systems, in particular electrically operated smoking systems.

One type of aerosol-generating system is an electrically operated smoking system. Handheld electrically operated smoking systems consisting of a device portion comprising a battery and control electronics, and a cartridge portion comprising a supply of aerosol-forming substrate, and an electrically operated vapouriser, are known. A cartridge comprising both a supply of aerosol-forming substrate and a vapouriser is sometimes referred to as a "cartomiser". The vapouriser typically comprises a coil of heater wire wound around an elongate wick soaked in liquid aerosol-forming substrate. Capillary material soaked in the aerosol-forming substrate supplies the liquid to the wisk. The cartridge portion typically comprises not only the supply of aerosol-forming substrate and an electrically operated vapouriser, but also a mouthpiece, which the user sucks on in use to draw aerosol into their mouth.

In some types of electrically operated aerosol-generating devices, a reservoir of aerosol-forming liquid is provided in a tank. In use in the aerosol-generating system, the liquid is conveyed from the tank by capillary action into the wick of a coil wick heater assembly where the liquid is vaporized. When a user draws at the mouthpiece an airstream flows over the heater assembly and the generated aerosol is inhaled by the user.

A problem of such a tank device is, that the system stops generating the aerosol if the device is held at such an angle that the liquid aerosol-generating substrate in the tank is not in contact with the capillary system. Moreover, these systems can be prone to leakage for example where the liquid from the tank floods the core or leaks through the airflow path.

In other systems, the liquid storage portion of a cartridge is filled with a capillary medium. The liquid aerosol-generating substrate is held in the capillary material and delivered to the wick. With such system the above mentioned problems of the holding angle and the risk of leakage can be reduced. However, some residual liquid will remain in the capillary material after usage, leading to wastage. Further, there can be an inconsistency in puff deliveries in such systems due to decreasing saturation of the capillary medium during usage, which does not allow for a constant high quality smoking experience.

It would be desirable to have a cartridge that avoids one or more of the above mentioned or other disadvantages, for example that avoids waste of aerosol-generating substrate liquid, preferably while maintaining or improving aerosol-generating performance of the aerosol-generating system, in which the cartridge is used.

According to a first aspect of the invention there is provided a cartridge for use in an aerosol-generating system, for example an electrically operated aerosol-generating system, comprising a liquid storage portion for holding a liquid aerosol-forming substrate. The liquid storage portion comprises at least two parts in fluid communication with each other. The first part of the liquid storage portion comprises a heater assembly, a first capillary material, provided in contact with the heater assembly, and a second capillary material in contact with the first capillary material and spaced apart from the heater assembly by the first capillary material. The second part of the liquid storage portion comprises a container for holding aerosol-forming substrate in liquid form and preferably arranged for supplying the liquid to the second capillary material. The second part of the liquid storage portion may comprise a tank that is substantially empty and is suitable for holding aerosol-forming substrate in liquid form.

The capillary material is preferably designed such that it is capable of holding sufficient liquid substrate for several puffs. As the capillary material is located in contact with the heater, the heater is provided independent of the holding angle of the aerosol-generating liquid with sufficient aerosol-generating liquid. The remaining inner volume of the liquid storage portion comprises no capillary material but represents an empty tank for storing aerosol-generating liquid. Under normal handling conditions an aerosol-generating medium, in particular an aerosol-generating smoking device, is transported between puffs and the capillary material will regularly contact and re-absorb new aerosol-generating liquid.

Because of the reduced amount of the capillary material used, the amount of residual liquid remaining in the capillary material after usage of the cartridge is smaller than in conventional cartridges in which the whole liquid storage portion is filled with capillary material. Moreover, performance tests have shown that the TPM (total particulate matter) yield of aerosol-generating smoking devices equipped with cartridges of the present invention is in many examples at least comparable to the performance of aerosol-generating smoking devices equipped with currently available cartridges.

Preferably the liquid capacity of the capillary material is such that it can hold enough liquid for 30 to 40 puffs or more. A 3 second puff may include about 1 mg to 4 mg of liquid, for example 3 mg to 4 mg of liquid. Preferably the capacity of the capillary material is between about 30 mg to about 160 mg, preferably 90 mg to about 160 mg or more, preferably 100 mg to 150 mg, for example 130 mg. Where there are two layers making up the capillary material, the capacity of the first and second layers may be such that about 10 to 20% by weight of the liquid capacity is in the first layer. For example, where the capacity of the capillary material is 30 puffs, the capacity of the first layer may be about 5 puffs, and the capacity of the second layer may be about 25 puffs.

Without wishing to be bound by any particular theory, it is thought that by the capillary material having capacity for several puffs, for example 30 or more puffs, the risk of leakage from the device is reduced. It is thought that if the capillary material is too small, then on puffing, liquid may be drawn from the reservoir straight through the capillary material and heater without being vapourised, leading to leakage. Also by having a capacity of 90 mg and more, a number of puffs can be taken from the device, even when the liquid in the reservoir is not in direct contact with the capillary material.

The heater assembly may be substantially flat and may comprise electrically conductive filaments, without the need for any winding of a heater wire around a capillary wick.

The electrically conductive filaments may lie in a single plane. A planar heater assembly can be easily handled during manufacture and provides for a robust construction.

The electrically conductive filaments may define interstices between the filaments and the interstices may have a width of between 10 μm and 100 μm. The filaments may give rise to capillary action in the interstices, so that in use, liquid to be vapourised is drawn into the interstices, increasing the contact area between the heater assembly and the liquid.

The electrically conductive filaments may form a mesh of size between 160 and 600 Mesh US (+/−10%) (i.e. between 160 and 600 filaments per inch (+/−10%)). The width of the interstices is preferably between 75 μm and 25 μm. The percentage of open area of the mesh, which is the ration of the area of the interstices to the total area of the mesh is preferably between 25 and 56%. The mesh may be formed using different types of weave or lattice structures. Alternatively, the electrically conductive filaments consist of an array of filaments arranged parallel to one another.

The electrically conductive filaments may have a diameter of between 10 μm and 100 μm, preferably between 8 μm and 50 μm, and more preferably between 8 μm and 39 μm. The filaments may have a round cross section or may have a flattened cross-section. The heater filaments may be formed by etching a sheet material, such as a foil. This may be particularly advantageous when the heater assembly comprises an array of parallel filaments. If the heater assembly comprises a mesh or fabric of filaments, the filaments may be individually formed and knitted together.

As described in relation to the first aspect, the heater assembly may comprise at least one filament made from a first material and at least one filament made from a second material different from the first material.

The heater assembly may comprise an electrically insulating substrate on which the filaments are supported, the filaments extending across an aperture formed in the substrate. The electrically insulating substrate may comprise any suitable material, and is preferably a material that is able to tolerate high temperatures (in excess of 300 degree Celsius) and rapid temperature changes. An example of a suitable material is a polyimide film, such as Kapton®.

The heater assembly may comprise an electrically conductive contact in contact with a plurality of the filaments. The electrically conductive contact may be provided between the housing of the liquid storage portion and the electrically insulating substrate. The electrically conductive contact may be provided between the filaments and the electrically insulating substrate. An aperture may be formed in the electrically insulating layer, and the cartridge may comprise two electrically conductive contacts positioned on opposite sides on the aperture to one another.

A capillary material is preferably a material that actively conveys liquid from one end of the material to another. The capillary material is advantageously oriented in the housing to convey liquid to the heater assembly.

The second capillary material may comprise a fibrous structure wherein the fibres are generally oriented in the direction of movement in the liquid to the heater. The first capillary material may have less oriented fibres. For example the first capillary material may have the structure of a felt.

The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heater. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The capillary material may be in contact with the heater, for example with the electrically conductive filaments. The capillary material may extend into interstices between the filaments. The heater assembly may draw liquid aerosol-forming substrate into the interstices by capillary action. The capillary material may be in contact with the electrically conductive filaments over substantially the entire extent of the aperture.

The housing may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material effectively acts as a spacer separating the heater element from the second capillary material so that the second capillary material is not exposed to temperatures above its thermal decomposition temperature. As used herein, "thermal decomposition temperature" means the temperature at which a material begins to decompose and lose mass by generation of gaseous by products. The second capillary material may advantageously occupy a greater volume than the first capillary material and may hold more aerosol-forming substrate that the first capillary material. The second capillary material may have superior wicking performance to the first capillary material. The second capillary material may be cheaper than the first capillary material. The second capillary material may be polypropylene.

The first capillary material can be selected from the group of kevlar felt, ceramic paper, ceramic felt, carbon felt, cellulose acetate, hemp felt, PET/PBT sheet, cotton pad, porous ceramic disc or porous metal disc.

Preferred materials include Kevlar felt, ceramic paper, ceramic felt, porous ceramic disc or porous metal disc. The first capillary material may comprise glass fibre paper or felt. Preferably the first capillary material includes substantially no organic matter.

Preferably the porosity of the first capillary material is less than that of the second capillary material. Preferably the pore size of the first capillary material is less than that of the second capillary material. The pore size may be for example measured as being an average pore size for a region of the capillary material. In this way it can be seen that the aerosol-generating substrate moves more efficiently to the heater. In a broad aspect of the invention, a cartridge is provided which includes a heater and a capillary material in contact with the heater for supplying aerosol-generating substrate to the heater, wherein the porosity or pore size of a region of the capillary material adjacent the heater is less than the porosity or pore size of a region of the capillary material remote from the heater. Thus a single material may be used, for example which has a gradient of pore size in one or more of its dimensions.

The first capillary material may have a fiber size/pore size of between 0.1 to 50 µm, preferably of between 0.5 to 10 µm and most preferably of about 4 µm. The first capillary material has a density of below 2 g/ml, and preferably of about 0.5 g/ml.

The second capillary material can be a so-called high retention material (HRM) material, selected from the group of polypropylene (PP), polyethylene (PE), polyphenylene sulphide (PPS), polyethylene terephthalate (PET), polybutylene terephthalate (PBT), rolled non-woven material or rolled felts. Preferably the second capillary material comprises a polymeric material. The material may include a coating, for example to reduce hydrophobicity.

The second capillary material may have a fiber size/pore size of between 1 to 100 µm, preferably of between 15 to 40 µm and most preferably of about 25 µm. The second capillary material may have a density of below 1 g/ml, and preferably of between 0.1 and 0.3 g/ml.

The first capillary material may separate the heater assembly from the second capillary material by a distance of at least 0.8 mm, for example at least 1.5 mm, and preferably between 0.8 mm and 2 mm in order to provide a sufficient temperature drop across the first capillary material.

The first and second capillary material can also be made from the same material, and can only be distinguished from each other in that they exhibit different porosities or different capillarity. For example the first capillary material can be compressed such that its pore size or porosity is reduced and its capillarity is increased compared to the second capillary material which may be used in an uncompressed or at least in a less compressed state.

In a preferred embodiment the first and the second material are made from a single continuous element of the same base material. More preferably the material is treated such that a gradient of pore size or porosity is obtained in a direction towards the heater element or the opening, such that the pore size or porosity decreases, for example continuously decreases, within the capillary material towards the heater element.

Preferably at least the first capillary material is compressed upon insertion into the first part of the housing of the liquid storage portion such that its effective pore size or porosity is reduced. For example the single continuous element may have the shape of a truncated cone, wherein the diameter of the circular base of the truncated cone is larger than the inner diameter of the cylindrical housing of the liquid storage portion, while the diameter of the truncated apex of the cone substantially corresponds to the inner diameter of the cylindrical housing of the liquid storage portion. Upon insertion the capillary material at the base of the cone of capillary material is more compressed than at the area of the truncated apex. The more compressed material represents the first capillary material and the less compressed material represents the second capillary material. The skilled artisan will readily appreciate that the resulting gradient of compression depends on the relative shape chosen for the capillary element and the housing of the liquid storage portion.

In a particularly preferred embodiment, the capillary element has a regular cylindrical shape with circular cross-section and a predefined diameter. The inner surface of the housing comprises a tapered portion at the opening end, such that the capillary material is compressed by this tapered portion upon insertion of the capillary material into the housing. Preferably the inner surface of the housing has a conical shape such that the inner diameter continuously increases from the open end towards the closed end of the cartridge.

The first capillary material and the second capillary material may comprise different regions of the same capillary material element. Compression of the capillary material when laced in the housing may be such that the pore size or porosity of the capillary material reduced or continuously reduces towards the heater assembly.

In a further embodiment the first and the second capillary material again are formed from a single continuous piece of the same material. The capillary material may be rectangular web of capillary material having a thickness that amounts to below 50%, preferably to about 25% of the inner diameter of the cylindrical housing of the cartridge. The width of the web of capillary material corresponds to the peripheral circumference of the housing. The web of capillary material can have any desired length and preferably is about half the length of the housing of the cartridge. The web of capillary material is rolled up to form a cylindrical shape. By rolling up, the central portion of the web is compressed to a higher degree than the outer portions of the web such that a gradient of pore size or porosity is obtained in radial direction of the rolled-up web of capillary material. In the middle the rolled-up capillary material an air channel is formed. A tube shaped fluid permeable heater element is provided in the air channel such that the heater is in direct contact with the inner surface of the rolled-up capillary material. Upon rolling up the capillary material the material portion that is closer to the center axis of the cylinder is more compressed than the material in the radial outward located portion of the capillary material. Thus, again a gradient of pore size is obtained, wherein the pore size of the capillary material is continuously decreased within the capillary material in the direction to the heater element. The capillary material is in fluid connection with a liquid reservoir, wherein the liquid reservoir is provided in the part of the housing that is not occupied by the capillary material. A partition is provided within the housing to ensure that the liquid substrate is not in direct communication with the air flow channel.

The web of capillary material may also comprise a plurality of layers of capillary material, such that the liquid retention properties of the capillary material can be designed in any desired way that is most suitable for the given aerosol-generating system.

In a particular preferred embodiment the heater element is rolled-up together with the capillary material, such that in only one manufacturing step a combined capillary material with radial gradient and included heating element is obtained.

The liquid storage portion may be positioned on a first side of the electrically conductive filaments and an airflow channel positioned on an opposite side of the electrically conductive filaments to the liquid storage portion, such that air flow past the electrically conductive filaments entrains vapourised liquid aerosol-forming substrate.

Preferably, the aerosol generating system comprises a housing. Preferably, the housing is elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle. The material may include PET, PBT or PPS.

Preferably, the aerosol-generating system is portable. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. The aerosol-forming substrate may comprise other additives and ingredients, such as flavourants.

Preferably the liquid storage portion comprises an opening and the heater assembly extends across the opening of the housing. The heater assembly may comprise an electrically insulating substrate on which the heater element is supported. The electrically insulating substrate may comprise any suitable material, and is preferably a material that is able to tolerate high temperatures (in excess of 300 degree Celsius) and rapid temperature changes. An example of a suitable material is a polyimide film, such as Kapton®. The electrically insulating substrate may have an aperture formed in it, with the heater element extending across the aperture. The heater assembly may comprise electrical contacts connected to the electrically conductive filaments.

According to a second aspect of the invention there is provided a cartridge for use in an aerosol-generating system, for example an electrically operated aerosol-generating system, with a liquid storage portion comprising a housing for holding a liquid aerosol-forming substrate, wherein the liquid storage portion comprises at least two parts in fluid communication to each other. The first part of the liquid storage portion comprises a first capillary material, provided at the vicinity of the opening of the housing, and a second capillary material in contact with the first capillary material and spaced apart from the opening by the first capillary material. The second part of the liquid storage portion may be substantially empty and being suitable for holding aerosol-forming substrate in liquid form.

The cartridge preferably further comprises a fluid permeable heater assembly extending across the opening of the housing.

In the embodiments of the present invention wherein the first part of the liquid storage portion occupies below 50%, preferably between 10% and 30%, more preferably between 15% and 25% and most preferably about 20% of the volume of the liquid storage portion.

The capillary material extends across the complete cross-section of the first part of the liquid storage portion, such that it is not possible for the liquid aerosol-generating substrate to flow directly to the heater assembly or the opening of the cartridge.

According to a further aspect of the invention there is provided an aerosol-generating system comprising a cartridge according to the present invention.

The system may further comprise electric circuitry connected to the heater assembly and to an electrical power source, the electric circuitry configured to monitor the electrical resistance of the heater assembly or of one or more filaments of the heater assembly, and to control the supply of power to the heater assembly dependent on the electrical resistance of the heater assembly or the one or more filaments.

The electric circuitry may comprise a microprocessor, which may be a programmable microprocessor. The electric circuitry may comprise further electronic components. The electric circuitry may be configured to regulate a supply of power to the heater assembly. Power may be supplied to the heater assembly continuously following activation of the system or may be supplied intermittently, such as on a puff-by-puff basis. The power may be supplied to the heater assembly in the form of pulses of electrical current.

The system advantageously comprises a power supply, typically a battery, within the main body of the housing. As an alternative, the power supply may be another form of charge storage device such as a capacitor. The power supply may require recharging and may have a capacity that allows for the storage of enough energy for one or more smoking experiences; for example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heater assembly.

Preferably, the aerosol generating system comprises a housing. Preferably, the housing is elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol-generating system is portable. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. The aerosol-forming substrate may comprise other additives and ingredients, such as flavourants.

Preferably the system comprises a mouthpiece, wherein the cartridge is inserted into the system in an orientation that the opening of the cartridge points away from the mouthpiece.

In another preferred embodiment the cartridge is inserted into the system in an orientation that the opening of the cartridge points towards the mouthpiece. Depending on the circumstances of usage one of these orientations of the cartridge may provide for superior performance compared to the other.

According to a further aspect of the invention there is provided a cartridge for use in an aerosol-generating system, comprising: a liquid storage portion comprising a housing for holding a liquid aerosol-forming substrate, the liquid storage portion comprising a heater assembly, and a capillary material, provided in contact with the heater assembly, wherein the average porosity or pore size of a region of the capillary material adjacent the heater assembly is smaller than the average porosity or pore size of a region of the capillary material remote from the heater assembly. A portion of the capillary material in the region may be compressed to reduce its porosity or pore size. The liquid storage portion may comprise at least two parts in fluid communication with each other, the first part of the liquid storage portion comprising the capillary material, and the second part of the liquid storage portion comprising a container for holding aerosol-forming substrate in liquid form and supplying the liquid to the higher porosity or pore size region of the capillary material.

The present invention is also directed to a method for manufacturing a cartridge for use in an electrically operated aerosol-generating system, comprising the steps of providing a liquid storage portion comprising a housing with a first part and a second part, providing heater assembly, placing a first capillary material in the first part of the housing of the liquid storage portion, such that first capillary material is provided in direct contact with the heater assembly, placing a second capillary material in the first part of the housing of the liquid storage portion, such that the second capillary material is in contact with the first capillary material and is spaced apart from the heater assembly by the first capillary material. The second part of the liquid storage portion is substantially empty and is suitable for holding aerosol-forming substrate in liquid form.

Preferably the first capillary material is compressed during or before insertion into the housing such that its pore size or porosity is reduced compared to the pore size or porosity in the relaxed state.

An aspect of the invention further provides a method of manufacture of a cartridge for use in an aerosol-generating system, comprising: providing a liquid storage portion comprising a housing, providing a heater assembly, placing a capillary material in the housing of the liquid storage portion, such that the capillary material is provided in direct contact with the heater assembly, wherein the method includes the step of compressing a portion of the capillary material during or before placing in the housing such that the porosity or pore size of the portion of the capillary material is reduced.

The invention also provides an aerosol-generating system as described herein being an electrically operated smoking system.

The term "substantially flat" filament arrangement preferably refers to a filament arrangement that is in the form of a substantially two dimensional topological manifold. Thus, the substantially flat filament arrangement extends in two dimensions along a surface substantially more than in a third dimension. In particular, the dimensions of the substantially flat filament arrangement in the two dimensions within the surface is at least 5 times larger than in the third dimension, normal to the surface. An example of a substantially flat filament arrangement is a structure between two substantially parallel surfaces, wherein the distance between these two surfaces is substantially smaller than the extension within the surfaces. In some embodiments, the substantially flat filament arrangement is planar. In other embodiments, the substantially flat filament arrangement is curved along one or more dimensions, for example forming a dome shape or bridge shape.

The term "filament" preferably refers to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term "filament arrangement" preferably refers to an arrangement of one or preferably a plurality of filaments. The filament arrangement may be an array of filaments, for example arranged parallel to each other. Preferably, the filaments may form a mesh. The mesh may be woven or non-woven.

It will be understood that, where appropriate, features of one aspect of the invention may be provided in relation to another aspect of the invention, in any appropriate combination.

The invention will be further described, by way of example only, with reference to the accompanying drawings in which.

Figures 1A, 1B:
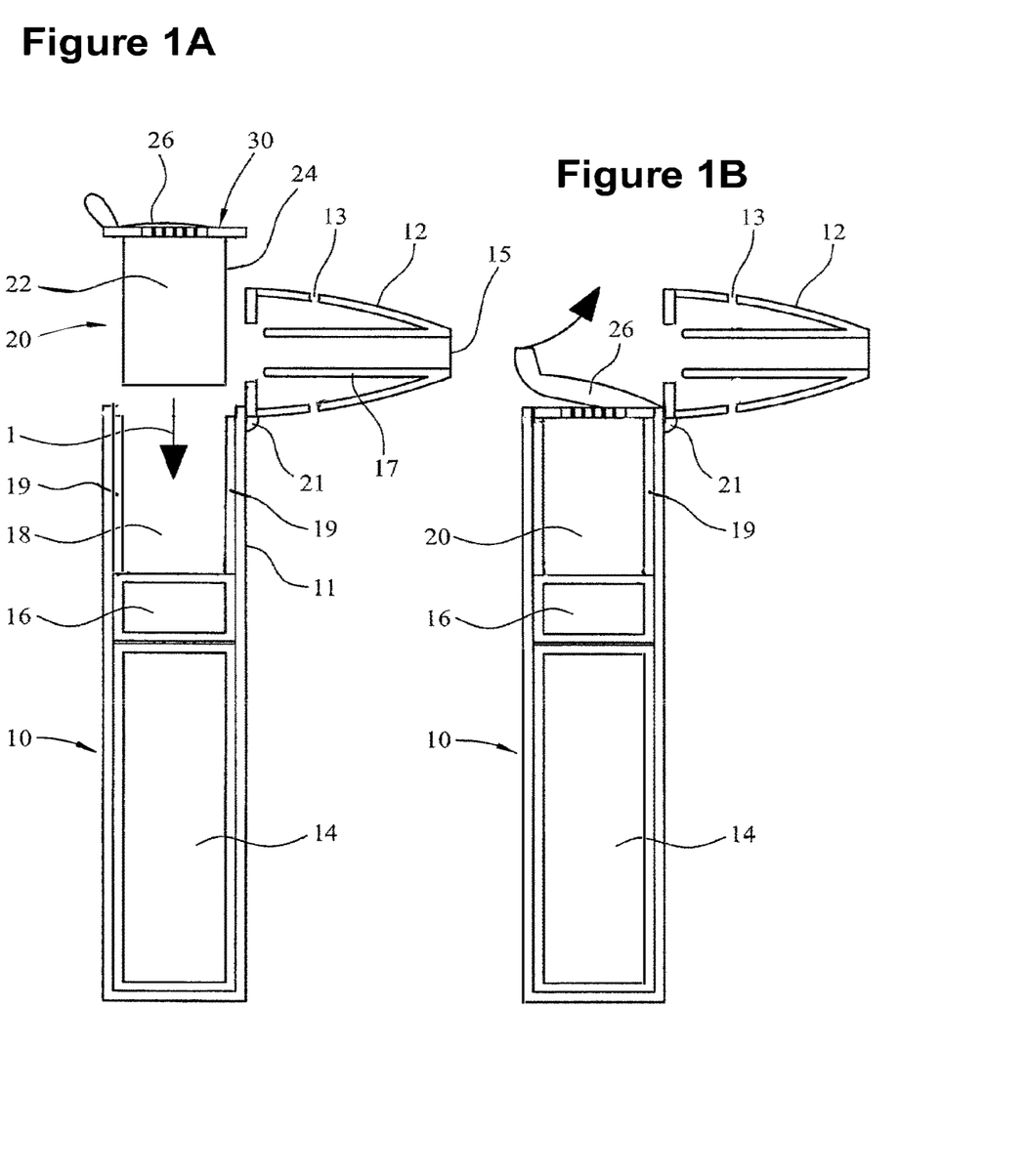
FIGS. 1a to 1d are schematic illustrations of a system, incorporating a cartridge, in accordance with an embodiment of the invention

FIGS. 1a to 1d are schematic illustrations of an aerosol-generating system, including a cartridge in accordance with an embodiment of the invention. FIG. 1a is a schematic view of an aerosol-generating device 10 and a separate cartridge 20, which together form the aerosol-generating system. In this example, the aerosol-generating system is an electrically operated smoking system.

The cartridge 20 contains an aerosol-forming substrate and is configured to be received in a cavity 18 within the device. Cartridge 20 should be replaceable by a user when the aerosol-forming substrate provided in the cartridge is depleted. FIG. 1a shows the cartridge 20 just prior to insertion into the device, with the arrow 1 in FIG. 1a indicating the direction of insertion of the cartridge.

Figure 1C:
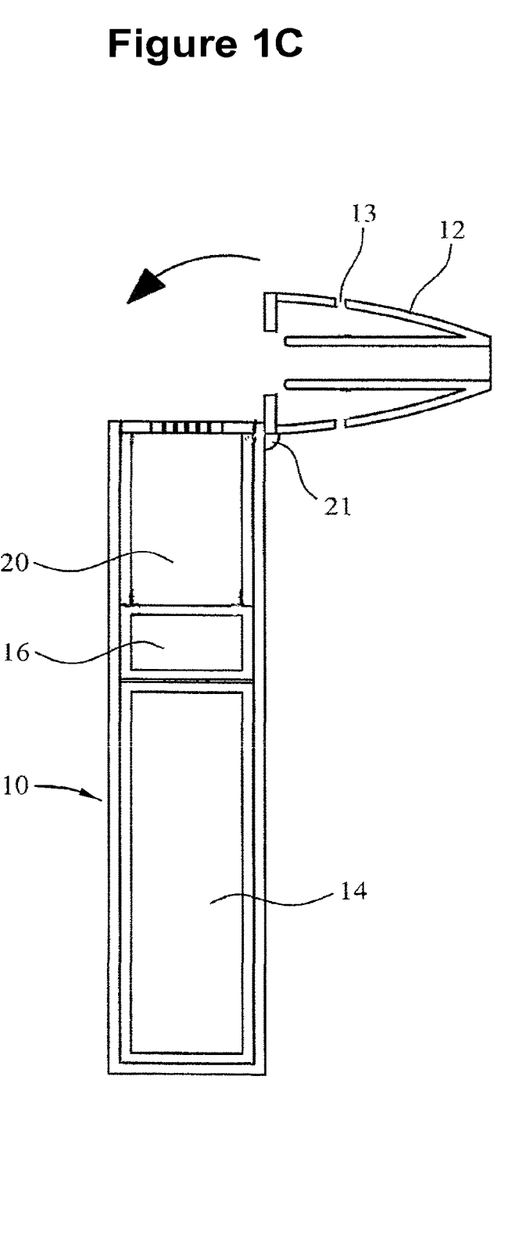
Figure 1D:
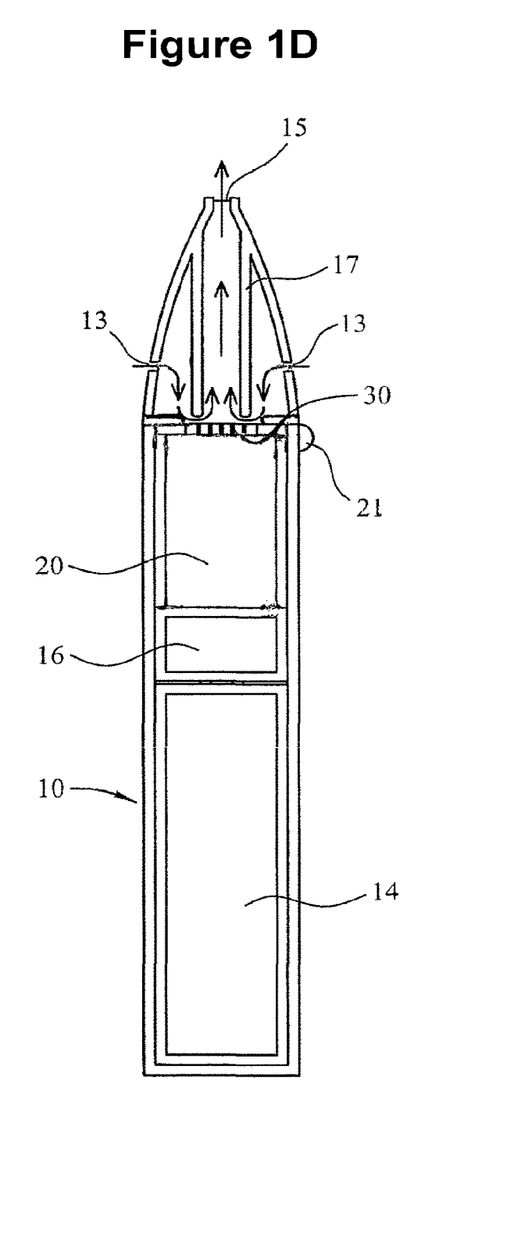

The aerosol-generating device 10 is portable and has a size comparable to a conventional cigar or cigarette. The device 10 comprises a main body 11 and a mouthpiece portion 12. The main body 11 contains a battery 14, such as a lithium iron phosphate battery, control electronics 16 and a cavity 18. The mouthpiece portion 12 is connected to the main body 11 by a hinged connection 21 and can move between an open position as shown in FIGS. 1a to 1c and a closed position as shown in FIG. 1d. The mouthpiece portion 12 is placed in the open position to allow for insertion and removal of cartridges 20 and is placed in the closed position when the system is to be used to generate aerosol, as will be described. The mouthpiece portion comprises a plurality of air inlets 13 and an outlet 15. In use, a user sucks or puffs on the outlet to draw air from the air inlets 13, through the mouthpiece portion to the outlet 15, and thereafter into the mouth or lungs of the user. Internal baffles 17 are provided to force the air flowing through the mouthpiece portion 12 past the cartridge, as will be described.

The cavity 18 has a circular cross-section and is sized to receive a housing 24 of the cartridge 20. Electrical connectors 19 are provided at the sides of the cavity 18 to provide an electrical connection between the control electronics 16 and battery 14 and corresponding electrical contacts on the cartridge 20.

FIG. 1b shows the system of FIG. 1a with the cartridge inserted into the cavity 118, and the cover 26 being removed. In this position, the electrical connectors rest against the electrical contacts on the cartridge, as will be described.

FIG. 1c shows the system of FIG. 1b with the cover 26 fully removed and the mouthpiece portion 12 being moved to a closed position.

FIG. 1d shows the system of FIG. 1c with the mouthpiece portion 12 in the closed position. The mouthpiece portion 12 is retained in the closed position by a clasp mechanism, The mouthpiece portion 12 in a closed position retains the cartridge in electrical contact with the electrical connectors 19 so that a good electrical connection is maintained in use, whatever the orientation of the system is. The mouthpiece portion 12 may include an annular elastomeric element that engages a surface of the cartridge and is compressed between a rigid mouthpiece housing element and the cartridge when the mouthpiece portion 12 is in the closed position. This ensures that a good electrical connection is maintained despite manufacturing tolerances.

Of course other mechanisms for maintaining a good electrical connection between the cartridge and the device may, alternatively or in addition, be employed. For example, the housing 24 of the cartridge 20 may be provided with a thread or groove (not illustrated) that engages a corresponding groove or thread (not illustrated) formed in the wall of the cavity 18. A threaded engagement between the cartridge and device can be used to ensure the correct rotational alignment as well as retaining the cartridge in the cavity and ensuring a good electrical connection. The threaded connection may extend for only half a turn or less of the cartridge, or may extend for several turns. Alternatively, or in addition, the electrical connectors 19 may be biased into contact with the contacts on the cartridge.

Other cartridge designs incorporating a capillary material arrangement in accordance with this disclosure can now be conceived by one of ordinary skill in the art. For example, the cartridge may include a mouthpiece portion, may include more than one heater assembly and may have any desired shape. Furthermore, a capillary assembly in accordance with the disclosure may be used in systems of other types to those already described, such as humidifiers, air fresheners, and other aerosol-generating systems The exemplary embodiments described above illustrate but are not limiting. In view of the above discussed exemplary embodiments, other embodiments consistent with the above exemplary embodiments will now be apparent to one of ordinary skill in the art.

Figure 2:
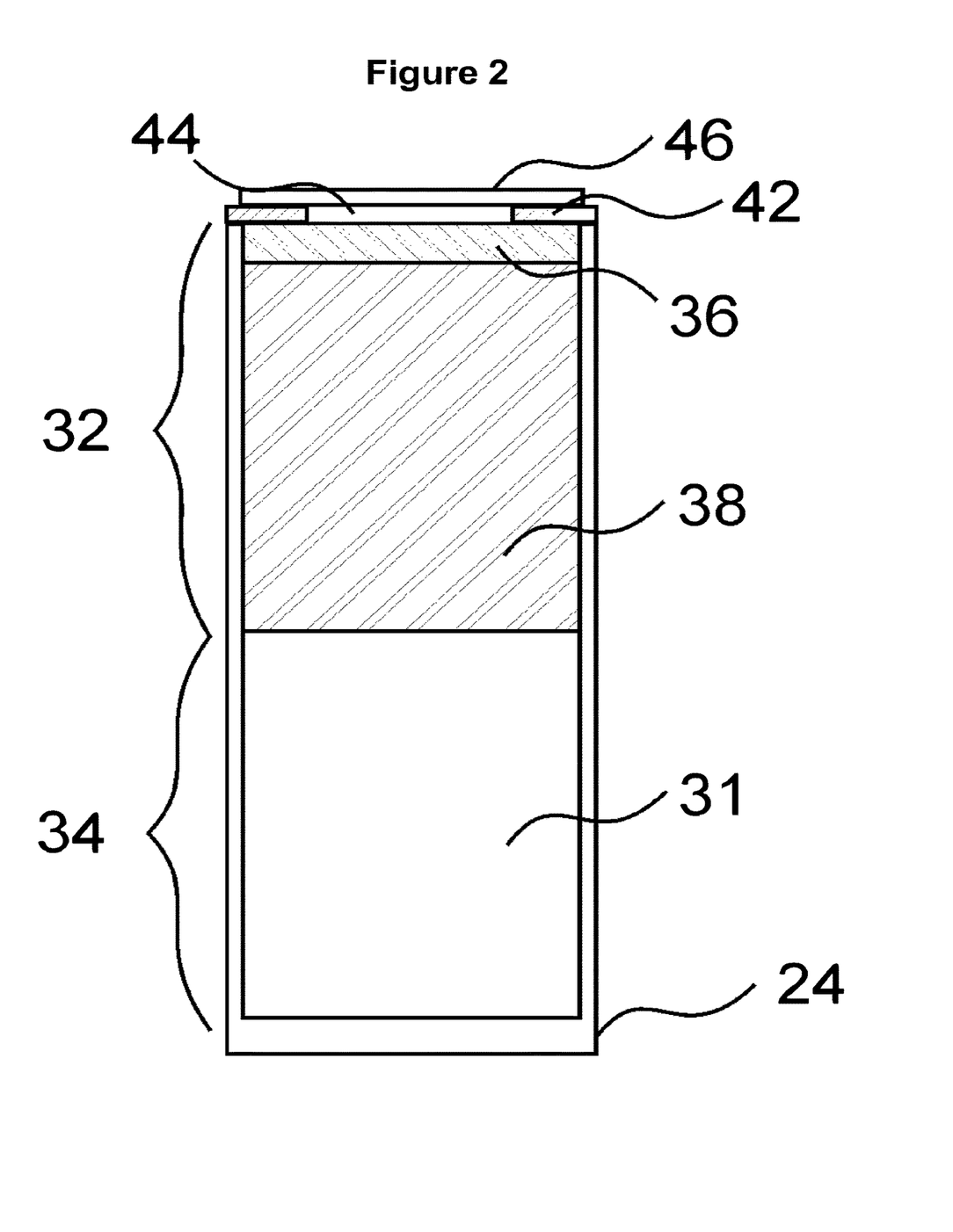
FIG. 2 shows a cartridge with porous medium according to a first aspect of the present invention.

The cartridge shown in FIG. 2 comprises a housing 24 made from polypropylene, with a two-part liquid storage portion. The first part 32 of the liquid storage portion comprises a first capillary material 36 and a second capillary material 38. The second part 34 of the liquid storage portion is an empty tank that can be filled or partly filled with liquid aerosol-generating substrate.

At the upper end of the cartridge a ceramic substrate 42 is provided. The substrate 24 defines an opening 44 and has electric contacts (not shown) at opposite sides thereof. A heater element 46 is connected to the electrical contacts of the substrate 32 and extends over the opening 44 defined by the substrate.

Both the first capillary material 36 and the second capillary material 38 retain liquid aerosol-forming substrate. The first capillary material 16, which is in direct contact with the heater element 46, has a higher thermal decomposition temperature (at least 160 degree Celsius or higher such as approximately 250 degree Celsius) than the second capillary material 38. The first capillary material 36 effectively acts as a spacer separating the heater element 46 from the second capillary material 38 so that the second capillary material 38 is not exposed to temperatures above its thermal decomposition temperature. The thermal gradient across the first capillary material 36 is such that the second capillary material 38 is exposed to temperatures below its thermal decomposition temperature. The second capillary material 38 may be chosen to have superior wicking performance to the first capillary material 36, may retain more liquid per unit volume than the first capillary material 36 and may be less expensive than the first capillary material 36. In this example the first capillary material 36 is a heat resistant material, such as a fiberglass or fiberglass containing material and the second capillary material 38 is a polymer such as high density polyethylene (HDPE), or polyethylene terephthalate (PET).

Figure 3:
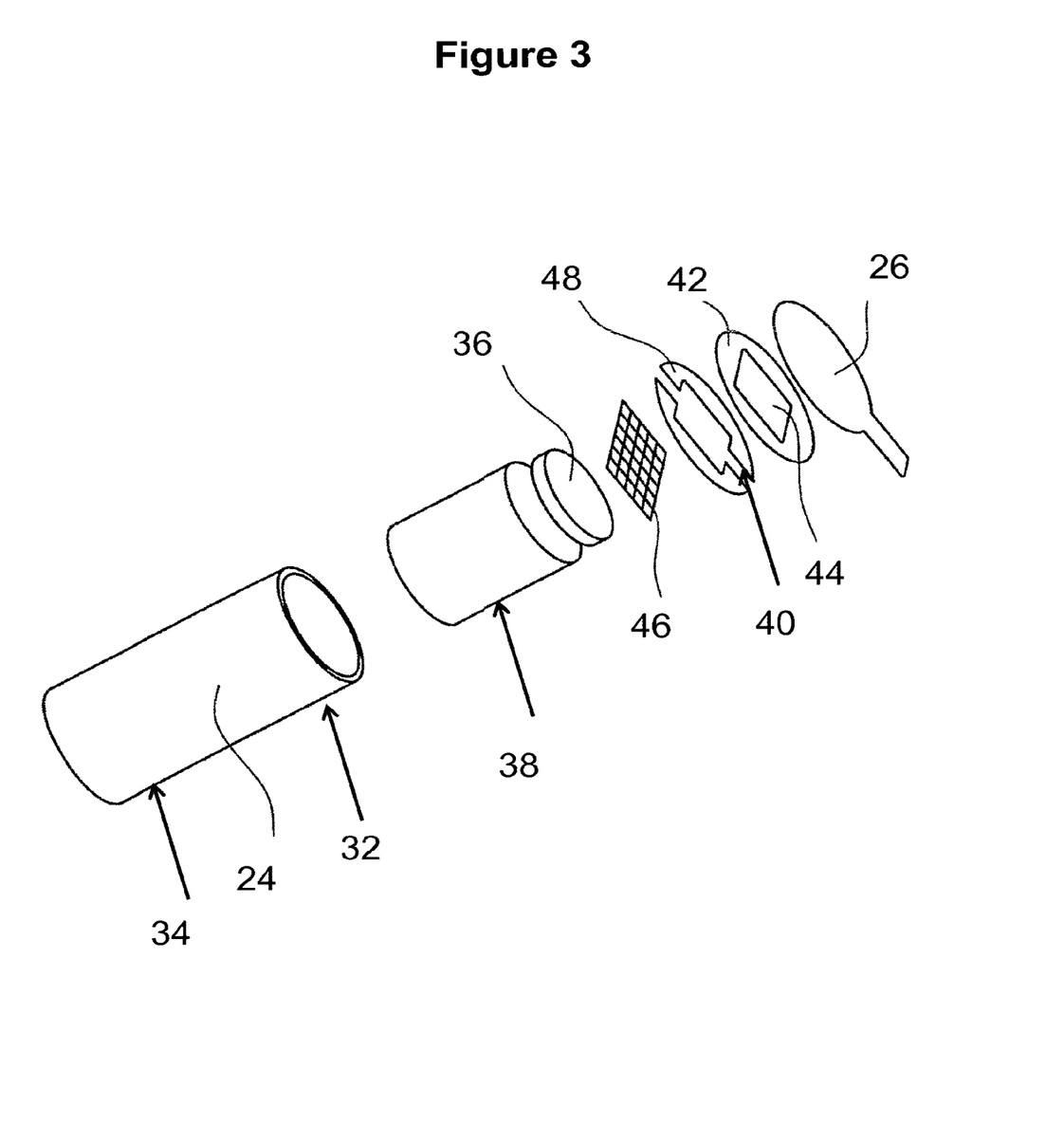
FIG. 3 shows an exploded view of a similar cartridge as shown in FIG. 2.

FIG. 3 is an exploded view of a cartridge similar to the cartridge of FIG. 2. The cartridge comprises a generally circular cylindrical housing 24 comprising a first part 32 and a second part 34. The first part of the housing 24 contains a first and a second capillary material 36, 38 that are soaked in a liquid aerosol-forming substrate. In this example the aerosol-forming substrate comprises 39% by weight glycerine, 39% by weight propylene glycol, 20% by weight water and flavourings, and 2% by weight nicotine. A capillary material here is a material that actively conveys liquid from one end to another, and may be made from any suitable material. In this example the capillary material is formed from polyester.

The housing 24 has an open end to which a heater assembly is fixed. The heater assembly comprises a substrate 42 having an aperture 44 formed in it, a pair of electrical contacts 48 fixed to the substrate 42 and separated from each other by a gap 40, and an resistive heater element 46 extending over the aperture 44 and being fixed to the electrical contacts 48 on opposing sides of the aperture 44.

The heater assembly is covered by a removable cover 26. The cover 26 comprises a liquid impermeable plastic sheet that is glued to the heater assembly but which can be easily peeled off. A tab is provided on the side of the cover to allow a user to grasp the cover when peeling it off. It will now be apparent to one of ordinary skill in the art that although gluing is described as the method to a secure the impermeable plastic sheet to the heater assembly, other methods familiar to those in the art may also be used including heat sealing or ultrasonic welding, so long as the cover may easily be removed by a consumer.

Figure 4:
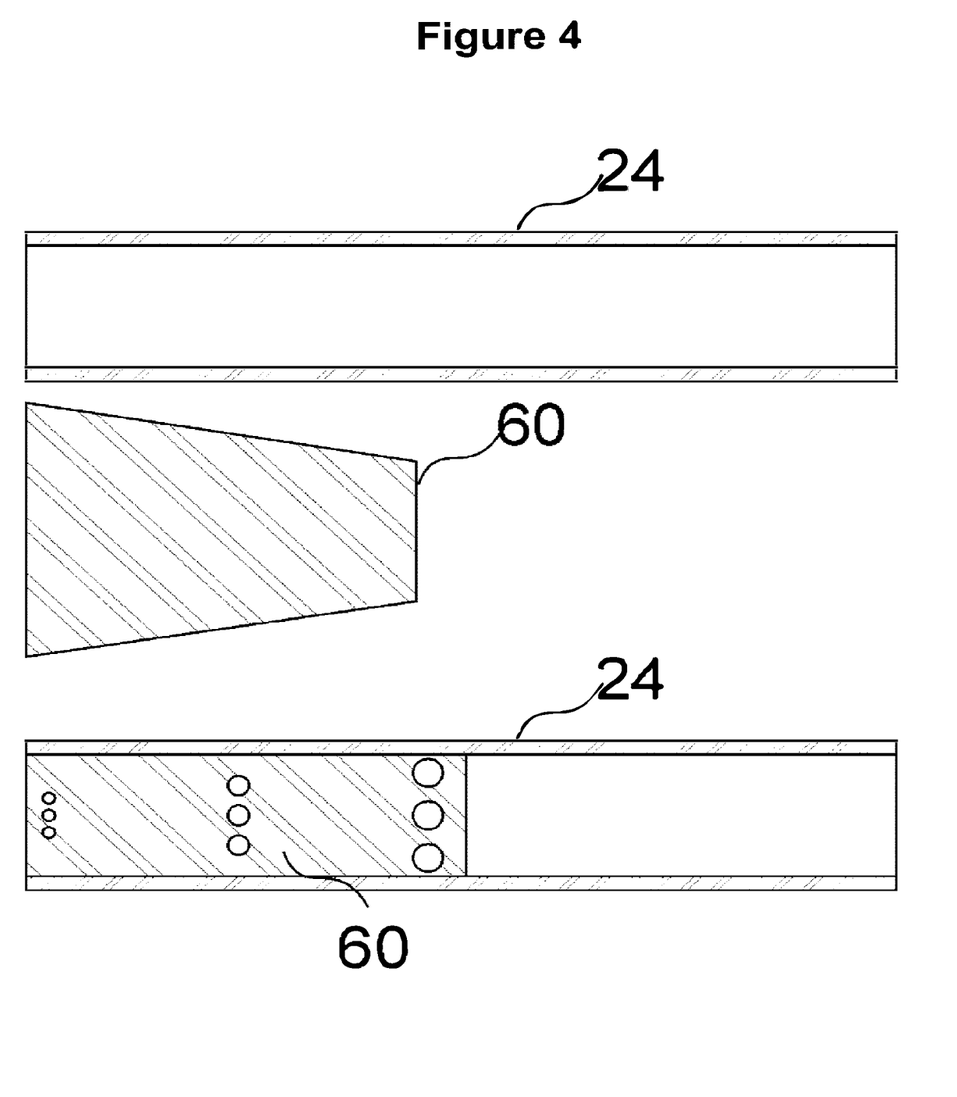
FIG. 4 shows a cartridge with a single porous medium compressed by the shape of porous material upon insertion into the housing.

FIG. 4 shows an embodiment wherein the housing 24 has the shape of a regular cylinder with circular cross-section. The first and the second capillary material are made from the same material and are integrally formed as single continuous piece of capillary material 60 having the shape of a truncated cone. The diameter of the truncated apex of the cone corresponds to the inner diameter of the cylindrical housing. The diameter of the base of the cone is twice as large as the inner diameter of the cylindrical housing. The capillary material 60 is inserted apex first into the cylindrical housing 24 until the surface of the base of the cone lies flush with the front face of the cylindrical housing. Upon insertion the capillary material 40 is compressed, whereby due to the relative shape of the capillary material and the cylindrical housing, compression of the capillary material 60 is increased towards end face of the cylindrical housing. At the same time pore size or porosity of the capillary material is reduced such that the pore size or porosity of the capillary material in the vicinity of the end face of the housing is smaller than the pore size or porosity of the capillary material located in the center of the cylindrical housing. The open end of the cylindrical housing at the right hand side in FIG. 4 is provided with a closure, such that the inside of the cylindrical housing forms a tank reservoir for holding liquid aerosol-generating substrate. At the other end the heater assembly as illustrated in FIGS. 2 and 3 can be provided.

Figure 5:
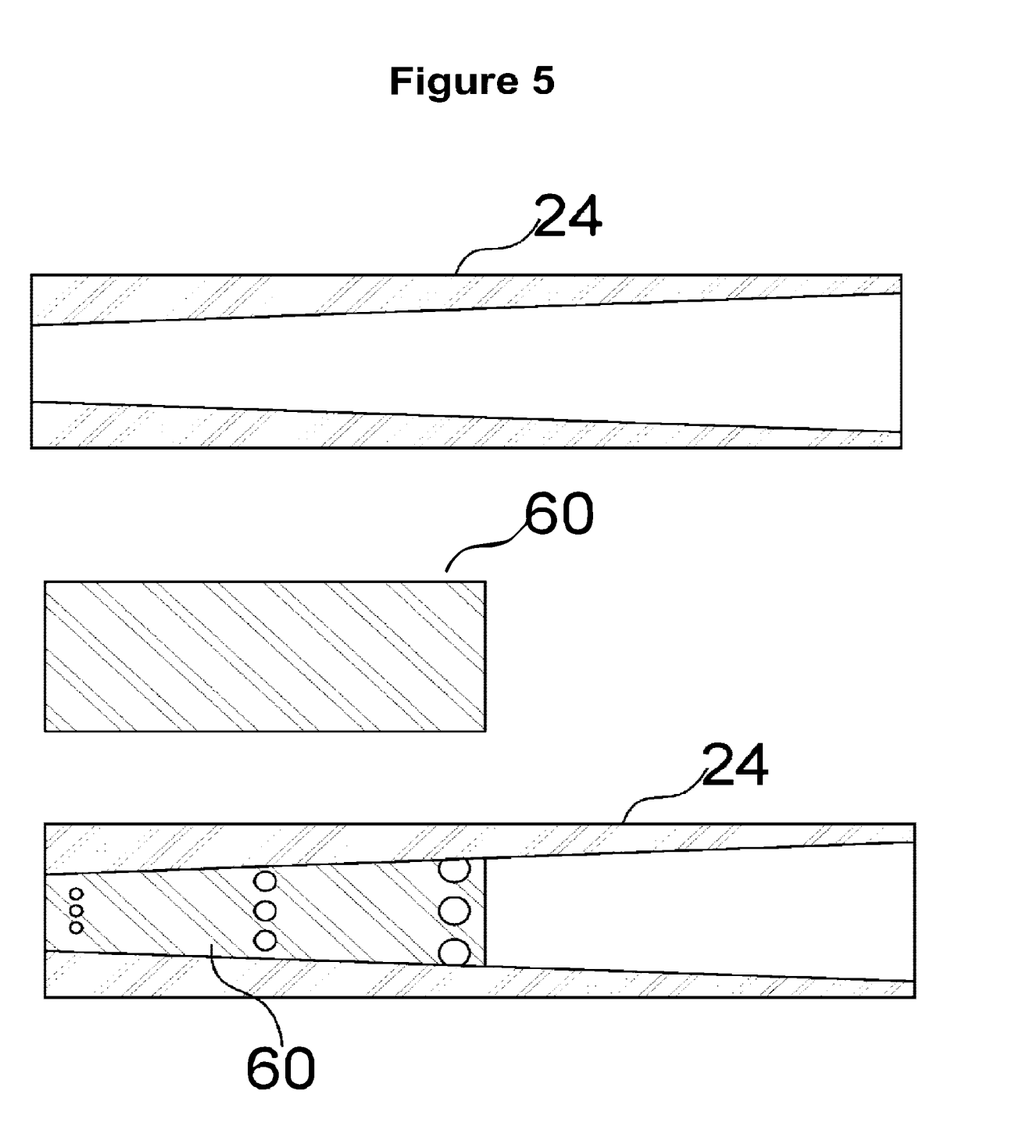
FIG. 5 shows a cartridge with a single porous medium compressed by the shape of inner surface of the housing upon insertion into the housing.

FIG. 5 shows an alternative embodiment having a similar effect as the embodiment depicted in FIG. 4. In this case the inner surface of the housing is provided with a conical shape, such that the interior tapers towards one end of the housing 24. Here the inner diameter of housing 24 at the left hand side in FIG. 5 is half the inner diameter of housing 24 at the right hand side. Again the first and the second capillary material are made from the same material and are integrally formed as single continuous piece of capillary material 60. The piece of capillary material 60 has regular cylindrical form with a circular cross-section. The diameter cylindrical piece of capillary material 60 corresponds to the inner diameter of the housing 24 at the right hand side In FIG. 5. The capillary material 60 is inserted into the housing 24 until an end face of the capillary material 60 lies flush with the smaller diameter front face of the cylindrical housing, i.e with the end face at the left hand side of the housing 24. Again the capillary material 60 is compressed upon insertion, whereby due to the relative shape of the capillary material and the cylindrical housing, compression of the capillary material 60 is increased towards the left hand side end face of the cylindrical housing 24. At the same time pore size or porosity of the capillary is reduced such that the pore size or porosity of the capillary material 60 in the vicinity of the end face of the housing is smaller than the pore size or porosity of the capillary material 60 located in the center of the cylindrical housing. Again, the open end of the cylindrical housing at the right hand side in FIG. 5 is provided with a closure, such that the inside of the cylindrical housing forms a tank reservoir for holding liquid aerosol-generating substrate. At the other end face of the housing, the heater assembly as illustrated in FIGS. 2 and 3 can be provided.

Figure 6:
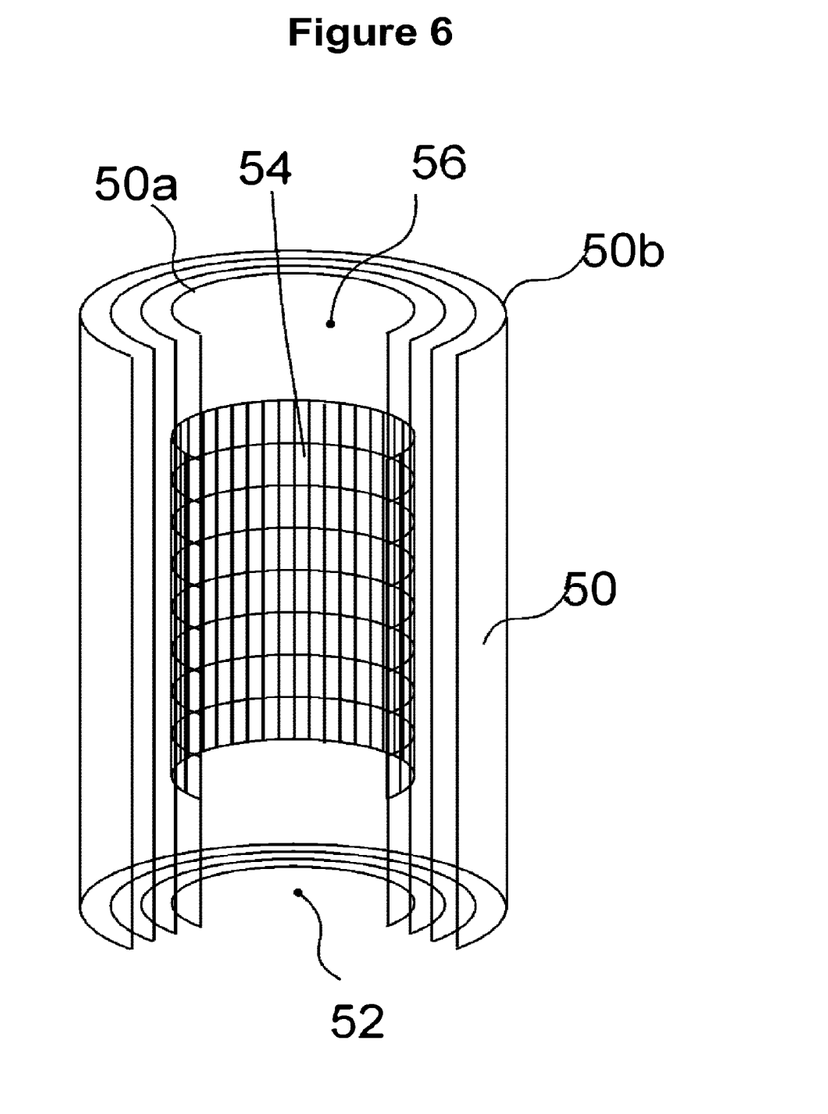
FIG. 6 shows a capillary material rolled-up into a cylindrical shape and being provided with a tube-shaped heater in the centre.

In FIG. 6 a further embodiment is depicted, whereby only the capillary material 50 that is to be used with a cylindrically housing is shown. The first and the second capillary material again are formed from a single continuous piece of the same material 50. The capillary material is a rectangular piece web of capillary material having a thickness that amounts to about 25% of the inner diameter of the cylindrical housing of the cartridge. The width of the web of capillary material corresponds to the peripheral circumference of the housing. The length of the web of capillary material is about half the length of the housing of the cartridge. The web of capillary material is rolled up to form a cylindrical shape. In the middle of the rolled-up capillary material an air channel 52 is formed. A tube shaped fluid permeable heater element 54 is provided in the air channel 52 such that the heater 54 is in direct contact with the inner surface 56 of the rolled-up capillary material 50. Upon rolling up the capillary material the material portion 50a that is closer to the center axis of the cylinder is more compressed than the material 50b in the radial outward located portion of the capillary material. Thus, again a gradient of pore size or porosity is obtained, wherein the pore size or porosity of the capillary material 50 is continuously decreased within the capillary material in the direction towards the heater element 54. The capillary material is in fluid connection with a liquid reservoir (not shown), wherein the liquid reservoir is provided in the part of the housing that is not occupied by the capillary material. A partition is provided within the housing to ensure that the liquid substrate is not in direct communication with the air flow channel 52.

It will be understood that different methods and configurations are possible to obtain the capillary material having a different pore size or porosity in different regions. In each example, a region of smaller pore size or porosity is located at one end of the capillary material. The region of smaller pore size or porosity is then located at the heater. The gradient in pore size or porosity then enhances the capillary action in the material, to draw aerosol-generating substrate liquid to the heater.

The invention claimed is:
1. A heater assembly for an aerosol-generating system, the heater assembly comprising:
   an electrically insulating support having an aperture;
   an electrical heating element disposed across the aperture in the electrically insulating support, being configured to heat a liquid aerosol-forming substrate to form an aerosol, and being substantially flat;
   capillary material, wherein a portion of the capillary material is in contact with the electrical heating element, and the capillary material is configured to convey the liquid aerosol-forming substrate to the electrical heating element; and
   two electrical contacts respectively connected to ends of the electrical heating element, the two electrical contacts supported by the electrically insulating support,
   wherein the capillary material is integrally formed as a single continuous piece of capillary material,
   wherein the capillary material comprises ceramic,
   wherein the two electrical contacts are provided on the ceramic, wherein the electrical heating element comprises one flat filament disposed in a curved manner between the two electrical contacts,
wherein the electrical heating element is fluid permeable, and
wherein the capillary material comprises:
a pore size of 0.5 to 10 μm and a density of below 2 g/ml, or
a pore size of 15 to 40 μm and a density of below 1 g/ml.

2. The heater assembly according to claim 1, wherein the one flat filament is curved along one or more dimensions thereof.

3. The heater assembly according to claim 1,
wherein the capillary material has a gradient of the pore size or porosity, such that the pore size or the porosity of the capillary material continuously decreases within the capillary material in a direction towards the electrical heating element.

4. The heater assembly according to claim 1, wherein the single continuous piece of capillary material comprises first and second capillary materials, the first capillary material includes the pore size of 0.5 to 10 μm and the density of below 2 g/ml, and the second capillary material includes the pore size of 15 to 40 μm and the density of below 1 g/ml.

5. The heater assembly according to claim 4,
wherein the first capillary material is in direct contact with the electrical heating element, and
wherein the second capillary material is in contact with the first capillary material and is separated from the electrical heating element by the first capillary material.

6. The heater assembly according to claim 4, wherein the first and the second capillary materials comprise different regions of a single continuous piece of capillary material.

7. The heater assembly according to claim 4, wherein the second capillary material is in fluid connection with the liquid aerosol-forming substrate.

8. The heater assembly according to claim 1, wherein the single continuous piece of capillary material has a shape of a truncated cone.

9. The heater assembly according to claim 8, wherein capillary material is in fluid connection with the liquid aerosol-forming substrate.

10. The heater assembly according to claim 1, wherein the capillary material is in fluid connection with the liquid aerosol-forming substrate.

11. The heater assembly according to claim 1, wherein the pore size is 4 μm and the density is 0.5 g/ml.

12. The heater assembly according to claim 1, wherein the pore size is 25 μm and the density is between 0.1 and 0.3 g/ml.

13. An aerosol-generating system, comprising:
an aerosol-generating device comprising a power source and a main body;
a cartridge removably inserted into the main body, the cartridge comprising:
a liquid storage portion configured to hold a liquid aerosol-forming substrate and comprising a housing including an air flow channel therein; and
a heater assembly comprising:
an electrically insulating support having an aperture,
an electrical heating element disposed across the aperture in the electrically insulating support, the electrical heating element being substantially flat,
capillary material, wherein a portion of the capillary material is in contact with the electrical heating element, and the capillary material is configured to convey the liquid aerosol-forming substrate to the electrical heating element, and
two electrical contacts respectively connected to ends of the electrical heating element, the two electrical contacts supported by the electrically insulating support; and
a mouthpiece comprising at least one air inlet and at least one air outlet,
wherein the capillary material is integrally formed as a single continuous piece of capillary material,
wherein the capillary material comprises ceramic,
wherein the two electrical contacts are provided on the ceramic,
wherein the electrical heating element comprises one flat filament disposed in a curved manner between the two electrical contacts,
wherein the electrical heating element is fluid permeable, and
wherein the capillary material comprises:
a pore size of 0.5 to 10 μm and a density of below 2 g/ml, or
a pore size of 15 to 40 μm and a density of below 1 g/ml.

14. The aerosol-generating system according to claim 13, wherein the pore size or porosity of the portion of the capillary material in contact with the electrical heating element is less than the pore size or porosity of the another portion of the capillary material separated from the electrical heating element by the portion of the capillary material in contact with the electrical heating element.

15. The aerosol-generating system according to claim 13, wherein the cartridge is between the main body and the mouthpiece.

16. The aerosol-generating system according to claim 13, wherein the one flat filament is curved along one or more dimensions thereof between the two electrical contacts respectively connected to ends of the one flat filament.

17. The aerosol-generating system according to claim 13, wherein the single continuous piece of capillary material has a shape of a truncated cone.

18. The aerosol-generating system according to claim 13, wherein the single continuous piece of capillary material comprises first and second capillary materials, the first capillary material includes the pore size of 0.5 to 10 μm and the density of below 2 g/ml, and the second capillary material includes the pore size of 15 to 40 μm and the density of below 1 g/ml.

19. An aerosol-generating system, comprising:
an aerosol-generating device comprising a power source and a main body;
a cartridge removably inserted into the main body, the cartridge comprising:
a liquid storage portion configured to hold a liquid aerosol-forming substrate and comprising a housing including an air flow channel therein; and
a heater assembly comprising:
an electrically insulating support having an aperture,
an electrical heating element disposed across the aperture in the electrically insulating support, the electrical heating element being substantially flat,
capillary material, wherein a portion of the capillary material is in contact with the electrical heating element, and the capillary material is configured to convey the liquid aerosol-forming substrate to the electrical heating element, and two electrical contacts respectively connected to ends of the electrical heating element, the two electrical contacts supported by the electrically insulating support; and a mouthpiece comprising at least one air inlet and at least one air outlet, wherein the heater assembly extends over an opening of the liquid storage portion, wherein the capillary material is integrally formed as a single continuous piece of capillary material, wherein the capillary material comprises ceramic, wherein the two electrical contacts are provided on the ceramic, wherein the electrical heating element is fluid permeable, and wherein the capillary material comprises:
  a pore size of 0.5 to 10 μm and a density of below 2 g/ml, or
  a pore size of 15 to 40 μm and a density of below 1 g/ml.

20. The aerosol-generating system according to claim 19, wherein the single continuous piece of capillary material comprises first and second capillary materials, the first capillary material includes the pore size of 0.5 to 10 μm and the density of below 2 g/ml, and the second capillary material includes the pore size of 15 to 40 μm and the density of below 1 g/ml.

* * * * *